United States Patent [19]

Rossetti et al.

[11] 4,217,276

[45] * Aug. 12, 1980

[54] RIFAMYCIN COMPOUNDS

[75] Inventors: Vittorio Rossetti; Leonardo Marsili; Carmine Pasqualucci, all of Milan, Italy

[73] Assignee: Archifar Laboratori Chimico Farmacologici S.p.A., Rovereto, Italy

[*] Notice: The portion of the term of this patent subsequent to Nov. 7, 1995, has been disclaimed.

[21] Appl. No.: 5,668

[22] Filed: Jan. 22, 1979

[30] Foreign Application Priority Data

Feb. 7, 1978 [GB] United Kingdom ................ 4773/78

[51] Int. Cl.$^2$ ........................................... C07D 497/18
[52] U.S. Cl. .......................... 260/239.3 P; 424/273 R
[58] Field of Search ................................. 260/239.3 P

[56] References Cited

U.S. PATENT DOCUMENTS 4,124,586  11/1978  Marsili et al. ................ 260/239.3 P

OTHER PUBLICATIONS

Kump et al., "Helv. Chim. Acta" vol. 56, pp. 2360-2362 and 2375-2377 (1973).

Primary Examiner—John M. Ford
Assistant Examiner—Robert T. Bond
Attorney, Agent, or Firm—Oblon, Fisher, Spivak, McClelland & Maier

[57] ABSTRACT

Rifamycin compounds having high antibacterial activity, consisting of powder colored from yellow to orange. Such compounds are provided by reacting 3-amino-rifamycin S with an aldehyde of formula X—CHO in the presence of a reducing agent and in an organic solvent.

2 Claims, No Drawings

RIFAMYCIN COMPOUNDS

This invention relates to novel Rifamycin compounds having high antibiotic activity.

The compounds according to the present invention have the following formula

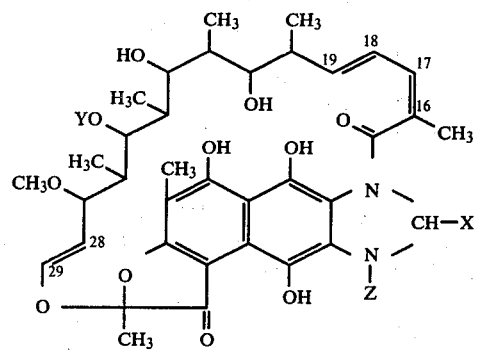

wherein:

Y is —H or —COCH$_3$

Z is, inter alia, propyl, allyl, hydroxy ethyl, cycloalkyl having from 3 to 6 carbon atoms, benzyl, phenyl, chlorophenyl, tetrahydrofurfuryl and their 16,17,18,19 tetrahydroderivatives and 16,17,18,19,28,29 hexahydroderivatives, X is hydrogen; alkyl having from 1 to 5 carbon atoms; cyclohexyl; alkenyl having 3 to 6 carbon atoms; cycloalkenyl having 6 carbon atoms; phenyl; phenyl substituted with a methoxy group; arylkenyl having 8 carbon atoms; a 5 member heterocycle having one heteroatom selected from the group consisting of O and S, substitution products for the above specified 5 member heterocycle having at least one radical selected from the group consisting of halogen and methyl; a 6 member heterocycle having one O heteroatom and their 16, 17,18,19 tetrahydroderivatives and 16,17,18,19,28,29 hexahydroderivatives and corresponding oxidized products having the formula

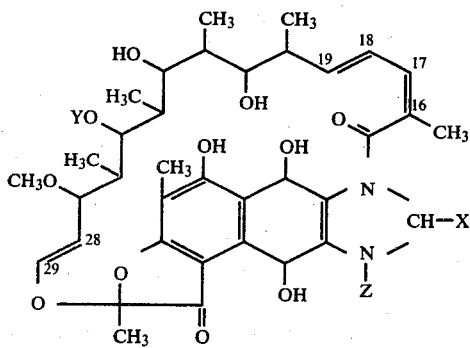

wherein X, Y and Z are as defined for formula (I) Products having formula similar to formula I and to formula II are described in the German patent application DOS 2651318 but the radical Z therein is only hydrogen.

Products of a similar structure are disclosed also in Helvetica Chimica Acta 56, p. 2360-62 and p. 2375-77(1973). However, such products differ from those of formula I and II by having the N atom at position 3 substituted with a methyl or ethyl group. These products are obtained by ultraviolet radiation of 3-dialkylamino-rifamycins S, and by such a method only compounds of formula (I) may be obtained having Z=ethyl and X=methyl or Z=methyl and X=hydrogen. It is well known to those skilled in the art that by reducing rifamycin S and its derivatives substituted at position 3, such as the 3-amino-rifamycins S of formula III, the corresponding rifamycins SV are obtained. In order to obtain the compounds of formula I and their 16,17, 18,19 tetrahydroderivatives and 16,17,18,19,28,29 hexahydroderivatives, an aldehyde of formula

X-CHO is reacted with a 3-amino-rifamycin S of formula

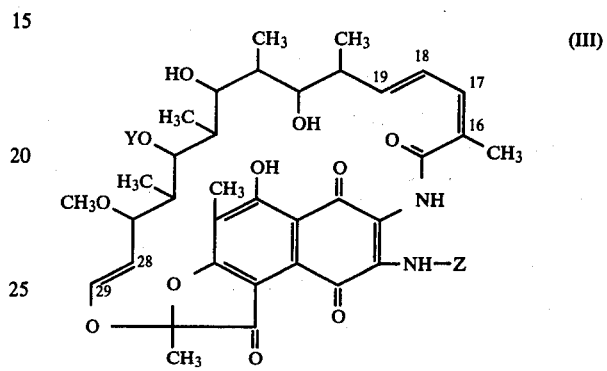

and their 16,17,18,19 tetrahydroderivatives and 16,17,18,19,28, 29 hexahydroderivatives.

X, Y and Z being as above defined, in the presence of a reducing agent selected from the group consisting of ascorbic acid, zinc and iron, in an organic solvent selected from the group consisting of dichloromethane, chloroform, tetrahydrofurane, dioxane, dimethylsulfoxide and N,N-dimethylformamide, at a temperature from 0° C. to +70° C. and for a time from 5 minutes to 3 days. The 3-amino-rifamycin S of formula (III) are per se well known and are described in the German Patent specification No. 1,670,377. Obviously, to obtain the compounds of formula (I), the aldehyde of formula X-CHO may be reacted without using any reducing agents with the hydroquinonoid derivatives (namely the reduced forms) of the compounds having formula III, they too described in the German Patent No. 1,670,377. It is well known that respective 16,17,18,19 tetrahydroderivatives and 16, 17, 18, 19, 28, 29 hexahydroderivatives can be obtained from the rifamycin compounds, such derivatives having comparable characteristics to those of the compounds from which are derived: the method for obtaining such derivatives would be obvious to those skilled in the art and, for example, is described in the above mentioned German Patent No. 1,670,377 and in Experientia 20, 336, (1964).

All of the compounds of formula (I) according to the present invention are coloured from yellow to orange and have a very high antibiotic activity on gram-positive germs, gram-negative germs and Mycobacterium Tuberculosis.

In order that the present invention be more clearly understood, some unrestrictive exemplary ambodiments of the invention will now be described. Thin layer chromatographies are performed on Silica gel plates F$_{254}$, using as eluent the mixture benzene:methanol:ethylacetate (20:8:7). Infrared spectrums are performed in nujol mull.

EXAMPLE 1

5 g of 3-n-propylamino-rifamycin S are dissolved in 100 ml of tetrahydrofuran and reacted while stirring with 2 g of zinc powder and 3 g of p-toluen-sulfonic acid for 10 minutes keeping the temperature below 20° C. with a water bath, then 5 ml of acetaldehyde are added and the mixture stirred 30' at room temperature. After filtration of insoluble material, the solution is washed with a saturated solution of sodium sulfite, than with a saturated solution of sodium disulfite and finally with a saturated solution of sodium chloride, the tetrahydrofuran solution is dried over magnesium sulfate and evaporated to dryness at reduced pressure. The solid orange material is crystallized from benzene to give 4.8 g of pure product having formula (I), where X is methyl and Z is n-propyl. Rf. 0.76. The mass spectrum shows a peak at 356 corresponding to the chromophore moiety. The PMR spectrum (CDCl$_3$ solution, TMS as internal reference) shows the following peaks at δ: 0.09 (d, CH$_3$-C[H]), 0.69 (d, CH$_3$-C [H]), 0.87 (d, CH$_3$-C [H]), 0.97 (t, partially hidden, CH$_3$-C[H$_2$]), 1.03 (d,CH$_3$-C[H]), 1.44 (d,

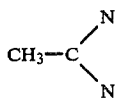

[H]), 1.78 (s,

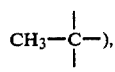

2.10 (s, CH$_3$- COO and

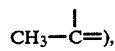

2.18 (s, CH$_3$-Ar), 3.12 (s, CH$_3$O), 4.95–5.45 (m, H-25,H-28 and

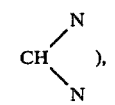

5.95–6.30 (m,H-17,H-18,H-19 and H-29), 11.60, 12.43 and 13.69 (s, 3 phenolic OH). Elemental analysis for C$_{42}$H$_{56}$N$_2$O$_{12}$.

|   | Calc. % | Found % |
|---|---|---|
| C | 64.51 | 64.61 |
| H | 7.35 | 7.07 |
| N | 3.58 | 3.55 |

Infrared spectrum 3500, 3150, 1715, 1650, 1590, 1545, 1343, 1315, 1255, 1240 (sh), 1206, 1163, 1150(sh), 1110, 1065, 1050, 1015, 970, 940, 930, 900 and 800 cm$^{-1}$.

Ultraviolet spectrum (CHCl$_3$): 456 nm (E$_1$ $_{cm}$$^{1\%}$ 118), 295 nm (E$_1$ $_{cm}$$^{1\%}$ 327), 238 nm (E$_1$ $_{cm}$$^{1\%}$ 323).

EXAMPLE 2

When in the reaction described in Example 1 acetaldehyde is replaced by aqueous formaldehyde, 5 g of product having formula (I), where X is hydrogen and Z is n-propyl, are obtained. Rf. 0.75.

Infrared spectrum: 3400(b), 1710, 1610, 1580, 1530, 1305, 1250, 1225, 1155, 1063, 1015 (sh), 970, 840, 895 and 800 cm$^{-1}$.

EXAMPLE 3

When in the reaction described in Example 1 acetaldehyde is replaced by thiophenaldehyde (2), 5 g of raw product are obtained. This material is purified by Silica gel column chromatography (250 g) (eluent benzene-:acetone 85:15) thus obtaining 2.2 g of pure product having formula (I), where X is 2-thienyl and Z is n-propyl.

Rf. 0.75

Infrared spectrum: 3425, 1710, 1655(sh), 1635, 1590, 1545, 1310, 1255, 1210, 1160, 1105, 1065, 1045, 1020(sh), 970, 945, 930(sh), 895, 855, 820 and 800 cm$^{-1}$.

Ultraviolet spectrum (CH$_3$OH): 459 nm (E$_1$ $_{cm}$ $^{1\%}$ 128); 321 nm (E$_1$ $_{cm}$$^{1\%}$ 262); 235 nm (E$_1$ $_{cn}$$^{1\%}$ 538).

Elemental analysis for C$_{45}$H$_{56}$N$_2$O$_{12}$S

|   | calc. % | found % |
|---|---|---|
| C | 63.66 | 62.61 |
| H | 6.65 | 6.72 |
| N | 3.30 | 3.05 |

EXAMPLE 4

When in the reaction described in Example 1 acetaldehyde is replaced by 5 ml of 5,6-dihydro-2H-pyran-3-aldehyde, a raw product is obtained that after Silica gel column chromatography (eluent benzene:acetone 85:15), 1.2 g of pure product having formula (I) where X is 5,6-dihydro-2H-3-pyryl and Z is n-propyl are obtained.

Rf 0.72

I.R.: 3500–3400, 1710, 1655, 1635, 1590, 1545, 1290, 1255, 1215, 1160, 1105, 1065, 975, 965 (sh), 945, 930, 895, 820 and 800 cm$^{-1}$.

U.V. (CH$_3$OH): 467 nm (E$_1$ $_{cm}$$^{1\%}$ 150); 319 nm (E$_1$ $_{cm}$$^{1\%}$ 288); 234 nm (E$_1$ $_{cm}$$^{1\%}$ 457)

Elemental analysis for C$_{46}$H$_{60}$N$_2$O$_{13}$

|   | calc. % | found % |
|---|---|---|
| C | 65.08 | 65.76 |
| H | 7.12 | 7.03 |
| N | 3.30 | 3.23 |

EXAMPLE 5

When in the reaction described in Example 1 acetaldehyde is replaced by furfural, and the reaction mixture is stirred for 30 hours, 5 g of raw material are obtained that, after column chromatography, as above described, give 1.7 g of pure orange product having formula (I), where X is 2-furyl and Z is n-propyl.

Rf. 0.70

U.V. (CH$_3$OH): 457 nm (E$_1$ $_{cm}$$^{1\%}$ 134); 319 nm (E$_1$ $_{cm}$$^{1\%}$ 285); 228 nm (E$_1$ $_{cm}$$^{1\%}$ 490)

Elemental analysis for C$_{45}$H$_{56}$N$_2$O$_{13}$

|   | calc. % | found % |
|---|---|---|
| C | 64.89 | 64.88 |

|   | calc. % | found % |
|---|---------|---------|
| H | 6.78    | 7.00    |
| N | 3.36    | 3.28    |

EXAMPLE 6

When in the reaction described in Example 1 acetaldehyde is replaced by isovalerialdehyde, 4.8 g of raw material are obtained, which are purified by column chromatography as above described, thus giving 2.3 g of pure product having formula (I), where X is isobuthyl and Z is n-propyl.

Rf 0.77

I.R.: 3450, 1715, 1660, 1635, 1590, 1545, 1320, 1265, 1210, 1165, 1125, 1100, 1060, 1050, 1015, 970, 940, 930(sh), 890 and 800 cm$^{-1}$.

U.V. (CH$_3$OH): 445 nm (E$_1$ $_{cm}$$^{1\%}$ 128); 314 nm (E$_1$ $_{cm}$$^{1\%}$ 240); 225 nm (E$_1$ $_{cm}$$^{1\%}$ 376).

Elemental analysis: for C$_{45}$H$_{62}$N$_2$O$_{12}$

|   | calc. % | found % |
|---|---------|---------|
| C | 65.67   | 66.38   |
| H | 7.59    | 7.94    |
| N | 3.40    | 3.28    |

EXAMPLE 7

When in the reaction described in Example 1 acetaldehyde is replaced by cinnamaldehyde and the reaction mixture is stirred for 5 hours at room temperature, 5 g of raw material are obtained that after crystallization from methanol, give 3.8 g of pure orange product having formula (I), where X is phenylvinyl and Z is n-propyl.

Rf 0.8

I.R.: 3400, 1710, 1655(sh), 1630, 1590, 1545, 1255, 1215, 1165, 1105, 1065, 970, 940, 930, 895 and 800 cm$^{-1}$.

U.V. (CHCl$_3$): 465 nm (E$_1$ $_{cm}$$^{1\%}$ 120); 259 nm (E$_1$ $_{cm}$$^{1\%}$ 530).

Elemental analysis: for C$_{49}$H$_{60}$N$_2$O$_{12}$

|   | calc. % | found % |
|---|---------|---------|
| C | 67.72   | 67.43   |
| H | 6.96    | 7.06    |
| N | 3.22    | 3.23    |

EXAMPLE 8

5 g of 3-cyclopropylamino-rifamycin S are dissolved in 50 ml of tetrahydrofuran and reacted with 2 g of zinc powder and 5 ml of acetic acid; the reaction mixture is stirred for 15 minutes at 20° C. and then 5 ml of acetaldehyde are added and stirred for further 30 minutes at room temperature. After filtration of insoluble material, the tetrahydrofuran solution is washed with a saturated solution of sodium sulfite, than with a saturated solution of sodium disulfite and finally with a saturated solution of sodium chloride, dried over magnesium sulfate and evaporated to dryness at reduced pressure; then crystallized from benzene to give 3.8 g of pure orange product having formula (I) where X is methyl and Z is cyclopropyl.

Rf. 0.78

I.R.: 3500, 3150, 1715, 1645, 1620, 1590, 1540, 1310, 1290, 1275, 1250, 1240, 1200, 1160, 1100, 1065, 1045, 1010, 965, 935, 900 and 790 cm$^{-1}$.

U.V. (CHCl$_3$): 452 nm (E$_1$ $_{cm}$$^{1\%}$ 117); 296 nm (E$_1$ $_{cm}$$^{1\%}$ 307); 242 nm (E$_1$ $_{cm}$$^{1\%}$ 356).

Elemental analysis: for C$_{42}$H$_{55}$N$_2$O$_{12}$

|   | calc. % | found % |
|---|---------|---------|
| C | 64.68   | 64.43   |
| H | 7.11    | 6.68    |
| N | 3.59    | 3.37    |

The same product is obtained using as solvent chloroform and the yields are similar.

EXAMPLE 9

3 g of 3-cyclopropylamino-rifamycin S are dissolved in 50 ml of dimethylsulfoxide and then reacted with 1 g of zinc powder, 10 ml of acetic acid and 3 g of paraformaldehyde; the reaction mixture is stirred for 1 hour at room temperature and filtereed. The solution is diluted with 10 ml of chloroform and washed several times with water; the chloroform solution is dried over sodium sulfate and evaporated to dryness at reduced pressure. The solid residue is triturated with petroleum ether and filtered, to give 2.3 g of pure product having formula (I) where X is hydrogen and Z is cyclopropyl.

Rf 0.74

I.R.: 3450, 1715(b), 1650(b), 1590, 1545, 1250(b), 1210, 1160, 1100, 1065, 1050, 1020, 970, 940, 900 and 800 cm$^{-1}$.

U.V. (CH$_3$OH): 450 nm (E$_1$ $_{cm}$$^{1\%}$ 123); 316 nm (E$_1$ $_{cm}$$^{1\%}$ 266); 226 nm (E$_1$ $_{cm}$$^{1\%}$ 413).

EXAMPLE 10

When in the reaction described in Example 8 acetaldehyde is replaced by isovalerialdehyde, 4.8 g of raw material are obtained that, purified by column chromatography as above described, give 3 g of pure product of formula (I) where X is isobutyl and Z is cyclopropyl.

Rf 0.77

I.R.: 3500, 1720, 1665, 1590, 1550, 1260, 1215, 1165, 1120, 1070, 1050, 1020, 975, 940(d), 900 and 800 cm$^{-1}$.

U.V. (CH$_3$OH): 447 nm (E$_1$ $_{cm}$$^{1\%}$ 115); 320 nm (E$_1$ $_{cm}$$^{1\%}$ 276); 230 nm (E$_1$ $_{cm}$$^{1\%}$ 437).

EXAMPLE 11

When in the reaction described in Example 8 acetaldehyde is replaced by 2-methyl-propanol, 4.5 g of product of formula (I) where X is isopropyl and Z is cyclopropyl are obtained.

Rf 0.78

I.R.: 3450, 1710, 1660, 1630, 1590, 1540, 1250, 1210, 1160, 1120, 1095, 1060, 1050, 1015, 970, 940, 890 and 795 cm$^{-1}$.

U.V. (CH$_3$OH): 445 nm (E$_1$ $_{cm}$$^{1\%}$ 109); 275 nm (E$_1$ $_{cm}$$^{1\%}$ 532).

EXAMPLE 12

When in the reaction described in Example 8 acetaldehyde is replaced by 2-methyl-pentanal, 5 g of product having formula (I) Where X is 2-methyl-buthyl and Z is cyclopropyl are obtained.

Rf 0.8

I.R.: ~3450, 1710, 1650, 1625, 1585, 1540, 1250, 1210, 1160, 1120, 1090, 1060, 1040(sh), 1015, 965, 940, 890 and 790 cm$^{-1}$.

U.V. (CH$_3$OH): 450 nm (E$_1$ $_{cm}$$^{1\%}$ 118); 320 nm (E$_1$ $_{cm}$$^{1\%}$ 254); 231 nm (E$_1$ $_{cm}$$^{1\%}$ 399).

EXAMPLE 13

When in the reaction described in Example 8 acetaldehyde is replaced by butanal, 5 g of raw material are obtained that after purification by column chromatography (as above described) give 3.5 g of pure product of formula (I) where X is propyl and Z is cyclopropyl.

Rf 0.73

I.R.: 3450, 1715, 1655, 1630, 1590, 1545, 1325, 1290, 1260, 1215, 1160, 1130, 1085, 1065, 975, 965, 945, 930, 890 and 790 cm$^{-1}$.

U.V. (CHCl$_3$): 455 nm (E$_1$ $_{cm}$$^{1\%}$ 108); 298 nm (E$_1$ $_{cm}$$^{1\%}$ 301); 243 nm (E$_1$ $_{cm}$$^{1\%}$ 364).

Elemental analysis for C$_{44}$H$_{59}$N$_2$O$_{12}$

|   | calc. % | found % |
|---|---------|---------|
| C | 65.41   | 65.40   |
| H | 7.36    | 7.40    |
| N | 3.47    | 3.24    |

EXAMPLE 14

When in the reaction described in Example 8 acetaldehyde is replaced by 2-ethyl-butanal, 4.8 g of product of formula (I) where X is 2-ethyl-propyl and Z is cyclopropyl are obtained. The same product is obtained using N,N-dimethyl-formamide as solvent.

Rf 0.83

I.R.: 3450, 1715, 1660, 1630, 1590, 1545, 1255, 1210, 1165, 1125, 1095, 1060 1045(sh), 1020, 970, 940, 890 and 795 cm$^{-1}$.

U.V. (CH$_3$OH): 450 nm (E$_1$ $_{cm}$$^{1\%}$ 115); 319 nm (E$_1$ $_{cm}$$^{1\%}$ 250); 229 nm (E$_1$ $_{cm}$$^{1\%}$ 392).

EXAMPLE 15

When in the reaction described in Example 8 acetaldehyde is replaced by hexanal, a raw product is obtained that, purified by column chromatography, gives 3.9 g of pure product having formula (I) where X is pentyl and Z is cyclopropyl.

Rf 0.79

I.R.: 3450, 1715, 1655, 1630, 1590, 1545, 1255, 1215, 1160, 1130, 1090, 1065, 1050(sh), 1020, 970, 945, 935, 895 and 795 cm$^{-1}$.

U.V. (CH$_3$OH): 451 nm (E$_1$ $_{cm}$$^{1\%}$ 128); 319 nm (E$_1$ $_{cm}$$^{1\%}$ 169); 229 nm (E$_1$ $_{cm}$$^{1\%}$ 416).

The same compound and the same yield is obtained using dioxane instead of tetrahydrofuran as solvent.

EXAMPLE 16

When in the reaction described in Example 8 acetaldehyde is replaced by 2-methyl-furfural, a raw product is isolated that is purified by column chromatography, to give 3 g of pure product of formula (I) where X is 2-methyl-5-furyl and Z is cyclopropyl.

Rf 0.72

I.R.: 3450, 1710, 1655, 1590, 1540, 1310, 1255, 1210, 1160, 1120, 1090, 1060, 1045(sh), 1020, 970, 940, 930, 890 and 795 cm$^{-1}$.

U.V. (CH$_3$OH): 451 nm (E$_1$ $_{cm}$$^{1\%}$ 118); 319 nm (E$_1$ $_{cm}$$^{1\%}$ 243); 230 nm (E$_1$ $_{cm}$$^{1\%}$ 501).

EXAMPLE 17

When in the reaction described in Example 8 acetaldehyde is replaced by 5,6-dihydro-2H-pyran-3-aldehyde, 4 g of raw product are obtained which are purified by column chromatography, to give 0.9 g of pure product of formula (I) where X is 2,6-dihydro-2H-3-pyryl and Z is cyclopropyl.

Rf 0.66

I.R.: 3500, 3450, 1710, 1660, 1630(b), 1595, 1550, 1290, 1255, 1215, 1160, 1130, 1110, 1070, 975, 950, 930, 900 and 800 cm$^{-1}$.

U.V. (CH$_3$OH): 450 nm (E$_1$ $_{cm}$$^{1\%}$ 133); 319 nm (E$_1$ $_{cm}$$^{1\%}$ 313); 229 nm (E$_1$ $_{cm}$$^{1\%}$ 521).

The compound is oxidized by means of manganese dioxide, to give the corresponding quinonoid structure that gives a correct elemental analysis: for C$_{46}$H$_{57}$N$_2$O$_{13}$

|   | calc. % | found % |
|---|---------|---------|
| C | 65.31   | 65.06   |
| H | 6.79    | 6.74    |
| N | 3.31    | 3.24    |

EXAMPLE 18

When in the reaction described in Example 8 acetaldehyde is replaced by 5-bromo-thiophen-2-aldehyde, a raw product is obtained that after column chromatography gives 0.3 g product having formula (I) where X is 5-bromo-thienyl (2) and Z is cyclopropyl.

Rf 0.65

I.R.: 3450, 1715, 1660, 1590, 1545, 1260, 1210, 1160, 1120, 1095, 1065, 1045, 1020, 970, 940, 890 and 800 cm$^{-1}$.

U.V. (CH$_3$OH): 450 nm (E$_1$ $_{cm}$$^{1\%}$ 122); 320 nm (E$_1$ $_{cm}$$^{1\%}$ 196); 234 nm (E$_1$ $_{cm}$$^{1\%}$ 405).

EXAMPLE 19

When in the reaction described in Example 8 acetaldehyde is replaced by thiophen-2-aldehyde, 3 g of product of formula (I) where X is 2-thienyl and Z is cyclopropyl are obtained.

Rf 0.73

I.R.: 3500, 3150, 1715, 1660, 1635, 1620, 1595, 1550, 1310, 1250, 1220, 1160, 1130, 1095, 1070, 1045, 1025, 975, 945, 935, 905, 860 and 800 cm$^{-1}$.

U.V. (CHCl$_3$): 458 nm (E$_1$ $_{cm}$$^{1\%}$ 114); 295 nm (E$_1$ $_{cm}$$^{1\%}$ 309); 243 nm (E$_1$ $_{cm}$$^{1\%}$ 434).

Elemental analysis: for C$_{45}$H$_{55}$N$_2$O$_{12}$S

|   | calc. % | found % |
|---|---------|---------|
| C | 63.74   | 64.13   |
| H | 6.54    | 6.62    |
| N | 3.30    | 3.22    |

EXAMPLE 20

When in the reaction described in Example 8 acetaldehyde is replaced by cinnamaldehyde, 2.1 g of compound having formula (I) where X is phenyl-vinyl and Z is cyclopropyl are obtained.

Rf 0.76

I.R.: ~3450(b), 1710, 1655, 1630, 1590, 1545, 1250, 1210, 1160, 1120, 1090, 1065, 1045(sh), 1020(sh), 970, 940, 890 and 795 cm$^{-1}$.

U.V. (CH$_3$OH): 450 nm (E$_1$ $_{cm}$$^{1\%}$ ;95); 319 nm (E$_1$ $_{cm}$$^{1\%}$ 212); 251 nm (E$_1$ $_{cm}$$^{1\%}$ 604).

EXAMPLE 21

3 g of 3-m-chloroanilino-rifamycin S are dissolved in 50 ml of tetrahydrofuran and, while stirring, are reacted with 1 g of zinc powder, 5 ml of acetic acid and with 3 ml of acetaldehyde. The reaction mixture is stirred at room temperature for 24 hours, filtered and the tetrahydrofuran solution is washed with a saturated solution of sodium sulfite, then with a saturated solution of sodium disulfite and finally with a saturated solution of sodium chloride, dried over magnesium sulfate and evaporated to dryness at reduced pressure. The residue is dissolved in 15 ml of benzene and chromatographied as above described to give 1.5 g of product having formula (I) where X is methyl and Z is m-chloro phenyl.

Rf. 0.68

I.R.: 3450, 1710, 1660, 1590, 1545, 1320, 1260, 1220, 1170, 1140, 1120, 1090, 1070, 1020-1010, 970, 950(sh), 925, 890, 865 and 800 cm$^{-1}$.

EXAMPLE 22

3 g of 3-anilino-rifamycin S are dissolved in 50 ml of tetrahydrofuran and, while stirring, are reacted with 1 g of zinc powder, 5 ml of acetic acid and 3 ml of acetaldehyde; the stirring is continued for 1 day at room temperature and the mixture is filtered, the tetrahydrofuran solution washed with a saturated solution of sodium sulfite, then with a saturated solution of sodium disulfite and finally with a saturated solution of sodium chloride, dried over magnesium sulfate and evaporated to dryness to give material that is purified by column chromatography as above described. 0.5 of pure product of formula (I) where X is methyl and Z is phenyl are obtained.

Rf. 0.72

EXAMPLE 23

5 g of 3-allylamino-rifamycin S are dissolved in 50 ml of tetrahydrofuran and reacted at room temperature, while stirring, with 2 g of zinc powder, 5 ml of acetic acid and 5 ml of acetaldehyde respectively; after 15 minutes the reaction mixture is filtered, and the tetrahydrofuran solution is washed with a saturated solution of sodium sulfite, sodium disulfite and sodium chloride respectively and dried over magnesium sulfate, filtered and evaporated to dryness at reduced pressure and finally crystallized from isopropylic alcohol, to give 3.3 g of pure product having formula (I) where X is methyl and Z is allyl.

Rf 0.73

I.R.: 3550, 3450, 3150, 1715, 1650, 1590, 1545, 1430, 1320, 1290, 1255, 1240(sh), 1205, 1165, 1150(sh), 1120, 1100, 1065, 1050, 1015, 975, 940, 930(sh), 910, 900, 885(sh), 860, 810, 770, 750 and 720 cm$^{-1}$.

U.V. (CHCl$_3$): 455 nm ($E_1$ $_{cm}$$^{1\%}$ 124); 296 nm ($E_1$ $_{cm}$$^{1\%}$ 331); 243 nm ($E_1$ $_{cm}$$^{1\%}$ 372).

Elemental analysis: for C$_{42}$H$_{55}$N$_2$O$_{12}$

|   | calc. % | found % |
|---|---------|---------|
| C | 64.68   | 64.48   |
| H | 7.11    | 7.24    |
| N | 3.59    | 3.48    |

EXAMPLE 24

When in the reaction described in Example 23 acetaldehyde is replaced by aqueous formaldehyde, 4.6 g of pure product of formula (I) (where X is hydrogen and Z is allyl) crystallize from tetrahydrofuran.

Rf. 0.73

I.R.: 3450, 1715, ~1640, 1590, 1550, 1260, 1245(sh), 1210, 1160, 1100(b), 1065, 1050, 1015, 975, 945, 930, 890 and 800 cm$^{-1}$.

U.V. (CH$_3$OH): 450 nm ($E_1$ $_{cm}$$^{1\%}$ 126); 318 nm ($E_1$ $_{cm}$$^{1\%}$ 278); 222 nm ($E_1$ $_{cm}$$^{1\%}$ 433).

EXAMPLE 25

When in the reaction described in Example 23 acetaldehyde is replaced by 2,6-dihydro-2H-pyran-3-aldehyde and stirred for 30 hours, a raw material is obtained that is purified by column chromatography as above described, to give 2.2 g of pure product of formula (I) where X is 2,6-dihydro-2H-pyryl (3) and Z is allyl.

Rf. 0.67

I.R.: 3500, 3400, 1705, 1655, 1630, 1590, 1545, 1340, 1310, 1290, 1255, 1210, 1155, 1125, 1105, 1060, 1040(sh), 970, 965, 940, 930, 910, 890, 820 and 795 cm$^{-1}$.

U.V. (CH$_3$OH): 450 nm ($E_1$ $_{cm}$$^{1\%}$ 129); 319 nm ($E_1$ $_{cm}$$^{1\%}$ 275); 232 nm ($E_1$ $_{cm}$$^{1\%}$ 443).

EXAMPLE 26

3.9 g of 3-allylamino-25-desacetyl-rifamycin S are dissolved in 50 ml of tetrahydrofuran and, at room temperature, are reacted, while stirring, with 1 g of zinc powder and 2 g of p-toluen sulfonic acid; the mixture is stirred for 10' and 3 ml of acetaldehyde are added. The reaction mixture is stirred 1 hour at room temperature and filtered; the tetrahydrofuran solution is washed with a saturated solution of sodium sulfite, sodium disulfite and sodium chloride respectively, dried over magnesium sulfate and evaporated to dryness at reduced pressure. The raw material such obtained is crystallized from methanol to give 1.4 g of pure product having formula (I) where X is methyl, Z is allyl and Y is hydrogen.

Rf. 0.62.

I.R.: 3350(b), 1650, 1620, 1580, 1535, 1325, 1245, 1200, 1150, 1090, 1060, 1045, 975, 960, 940, 905, 885, 850 and 795 cm$^{-1}$.

U.V. (CHCl$_3$): 459 nm ($E_1$ $_{cm}$$^{1\%}$ 129); 294 nm ($E_1$ $_{cm}$$^{1\%}$ 345); 242 nm ($E_1$ $_{cm}$$^{1\%}$ 378).

EXAMPLE 27

3 g of 3-n-propylamin-25-desacetyl-rifamycin S are dissolved in 50 ml of tetrahydrofuran and reacted, while stirring, with 1 g of zinc powder, 2 g of p-toluen sulfonic acid and 2 ml of isovalerialdehyde. The reaction mixture is stirred at room temperature for 12 hours and filtered, washed with a saturated solution of sodium sulfite, sodium disulfite and sodium chloride respectively dried and evaporated to dryness at reduced pressure: the residue is triturated in petroleum ether to give 2.9 g of product having formula (I) where X is isobutyl, Y is hydrogen and Z is n-propyl.

Rf. 0.61

I.R.: 3400(b), 1660, 1630, 1590, 1545, 1320, 1210, 1165, ~1110, 1055, 970, 940, 890 and 800 cm$^{-1}$.

U.V. (CH$_3$OH): 450 nm ($E_1$ $_{cm}$$^{1\%}$ 119); 319 nm ($E_1$ $_{cm}$$^{1\%}$ 273); 230 nm ($E_1$ $_{cm}$$^{1\%}$ 421).

EXAMPLE 28

When in the reaction described in Example 27 isovalerialdehyde is replaced by acetaldehyde 2 g of product of formula (I) where X is methyl Y hydrogen and Z is n-propyl are obtained.

Rf. 0.62

I.R.: 3400(b), 1655(sh), 1635, 1590, 1550, 1330, 1210, 1165, 1115, 1100, 1070, 1055, 970, 945, 895, 860, 805 and 795 cm$^{-1}$.

U.V. (CH$_3$OH): 455 nm ($E_1$ $_{cm}$$^{1\%}$ 130); 316 nm ($E_1$ $_{cm}$$^{1\%}$ 288); 229 nm ($E_1$ $_{cm}$$^{1\%}$ 470).

EXAMPLE 29

3 g of 3-cyclohexilamino-rifamycin S are dissolved in 50 ml of dioxane and reacted, while stirring, with 1 g of zinc powder, 2 g of p-toluenesulfonic acid and 3 ml of 35% aqueous formaldehyde. The reaction mixture is stirred for 3 hours at room temperature and filtered. The organic solution is diluted with 100 ml chloroform and washed with water several times; the chloroform solution is dried over sodium sulfate and evaporated to dryness at reduced pressure. The residue is purified by silica gel column chromatography, to give 1.5 g of pure product having formula (I) where X is hydrogen and Z is cyclohexyl.

Rf. 0.76

I.R.: 3450, 1710, 1630, 1590, 1540, 1255, 1210, 1160, 1125, 1095, 1065, 1015(sh), 970, 940, 930, 890 and 795 cm$^{-1}$.

U.V. (CH$_3$OH): 450 nm ($E_1$ $_{cm}$$^{1\%}$ 106); 318 nm ($E_1$ $_{cm}$$^{1\%}$ 232); 255 nm ($E_1$ $_{cm}$$^{1\%}$ 327); 220 nm ($E_1$ $_{cm}$$^{1\%}$ 364).

EXAMPLE 30

When in the reaction described in Example 29 formaldehyde is replaced by acetaldehyde, 1 g (after purification by column chromatography) of product having formula (I) where X is methyl and Z is cyclohexyl is obtained.

Rf. 0.74

I.R.: 3450, 1710, 1655(sh), 1630, 1590, 1540, 1320, 1255, 1210, 1160, 1130, 1090, 1065, 1010, 970, 940, 930, 895, 860, 805(sh) and 790 cm$^{-1}$.

U.V. (CH$_3$OH): 455 nm ($E_1$ $_{cm}$$^{1\%}$ 111); 320 nm ($E_1$ $_{cm}$$^{1\%}$ 259).

EXAMPLE 31

When in the reaction described in Example 1 acetaldehyde is replaced by crotonaldehyde, 3.5 g of pure product having formula (I) where X is 2-methylvinyl and Z is n-propyl are obtained (cristalized from ethanol).

Rf. 0.74

I.R.: 3500, 1710, 1655, 1635, 1590, 1545, 1400, 1260, 1210, 1155, 1125, 1105, 1090, 1065, 1050, 1015, 970, 940, 930, 890, 840 and 800 cm$^{-1}$.

U.V. (CHCl$_3$): 460 nm ($E_1$ $_{cm}$$^{1\%}$ 132); 318 mm ($E_1$ $_{cm}$$^{1\%}$ 276); 228 nm ($E_1$ $_{cm}$$^{1\%}$ 448).

EXAMPLE 32

When in the reaction described in Example 1 acetaldehyde is replaced by dimethylacrolein, 5 g of raw product are obtained, that after purification by column chromatography give 1.8 g of pure compound of formula (I) where X is 2,2-dimethylvinyl and Z is n-propyl.

Rf. 0.77

I.R.: 3450, 1715, 1655, 1635, 1590, 1545, 1255, 1210, 1160, 1120, 1105, 1065, 1050, 1015(sh), 970, 940, 930(sh), 895, 855 and 795 cm$^{-1}$.

U.V. (CH$_3$OH): 450 nm ($E_1$ cm$^{1\%}$ 140); 300 nm Shoulder; 226 nm ($E_1$ cm$^{1\%}$ 457).

EXAMPLE 33

When in the reaction described in Example 23 acetaldehyde is replaced by cinnamaldehyde, 3.6 g of pure product having formula (I) where X is phenylvinyl and Z is allyl are obtained (cristallized from isopropylalcohol).

Rf. 0.76

I.R.: 3450, 1710, 1660, 1630, 1590, 1545, 1315, 1260, 1215, 1160, 1125, 1105, 1090, 1065, 1050(sh), 1020, 970, 940, 930, 890, 865, 835, 805 and 795 cm$^{-1}$.

U.V. (CHCl$_3$): 450 nm ($E_1$ $_{cm}$$^{1\%}$ 134); 318 nm ($E_1$ $_{cm}$$^{1\%}$ 279); 253 nm ($E_1$ $_{cm}$$^{1\%}$ 544).

EXAMPLE 34

When in the reaction described in Example 8 acetaldehyde is replaced by 4-metoxy-benzaldehyde, 5 g of raw product are obtained; after purification by column chromatography as already described, we obtain 3.2 g of pure product of formula (I) where X is 4-methoxyphenyl and z is cyclopropyl.

Rf. 0.75

I.R.: 3500, 1730, 1650, 1630, 1590, 1540, 1510, 1290, 1240, 1200, 1170, 1160, 1090, 1050, 1040, 1020, 970, 950, 930, 890, 850, 820 and 790 cm$^{-1}$.

U.V. (CH$_3$OH): 445 nm ($E_1$ $_{cm}$$^{1\%}$ 127); 319 nm ($E_1$ $_{cm}$$^{1\%}$ 233); 229 nm ($E_1$ $_{cm}$$^{1\%}$ 448).

EXAMPLE 35

When in the reaction described in Example 8 acetaldehyde is replaced by cyclohexancarbaldehyde, a raw product is obtained that after purification gives 3.5 g of pure product having formula (I) where X is cyclohexyl and Z is cyclopropyl.

Rf. 0.76

I.R.: 3450, 1710, 1660, 1630, 1590, 1540, 1320, 1290, 1250, 1210, 1160, 1120, 1090, 1060, 1050(sh), 1020, 970, 940, 890 and 790 cm$^{-1}$.

U.V. (CH$_3$OH): 451 nm ($E_1$ $_{cm}$$^{1\%}$ 123); 319 nm ($E_1$ $_{cm}$$^{1\%}$ 290); 231 nm ($E_1$ $_{cm}$$^{1\%}$ 422).

EXAMPLE 36

When in the reaction described in Example 8 acetaldehyde is replaced by 3-cyclohexen-1-aldehyde we obtain 2.9 g of product having formula (I) where X is 3-cyclohexen-1-yl and Z is cyclopropyl.

Rf. 0.75

I.R.: 3400(b), 1710, 1660, 1630, 1590, 1550, 1520(sh), 1320, 1290, 1250, 1210, 1160, 1120, 1090, 1060, 1050, 1020, 970, 940, 890, 820 and 800 cm$^{-1}$.

U.V. (CH$_3$OH): 448 nm ($E_1$ $_{cm}$$^{1\%}$ 116); 317 nm ($E_1$ $_{cm}$$^{1\%}$ 281); 229 nm ($E_1$ $_{cm}$$^{1\%}$ 444).

EXAMPLE 37

When in the reaction described in Example 8 acetaldehyde is replaced by benzaldehyde, 4 g of product of formula (I) where X is phenyl and Z is cyclopropyl are obtained.

Rf. 0.72

I.R.: 3450(b), 1710, 1660, 1630, 1590, 1540, 1310, 1250, 1210, 1160, 1120, 1090, 1060, 1050, 1020, 970, 940, 930, 890, 830(b) and 790 cm$^{-1}$.

U.V. (CH$_3$OH): 450 nm ($E_1$ $_{cm}$$^{1\%}$ 131); 315 nm ($E_1$ $_{cm}$$^{1\%}$ 245).

EXAMPLE 38

When in the reaction described in Example 1 acetaldehyde is replaced by 2-methyl-butanal, 2.9 g of product of formula (I) where X is 2-butyl and Z is n-propyl are obtained.

Rf. 0.77

I.R.: 3450, 1710, 1660, 1630, 1590, 1540, 1340, 1320, 1250, 1210, 1160, 1150, 1120, 1100, 1070, 1050(sh), 1010, 970, 940, 890 and 800 cm$^{-1}$.

U.V. (CH$_3$OH): 451 nm (E$_1$ $_{cm}$$^{1\%}$ 128); 319 nm (E$_1$ $_{cm}$$^{1\%}$ 279); 229 nm (E$_1$ $_{cm}$$^{1\%}$ 410).

EXAMPLE 39

3.2 g of 3-benzyl-rifamycin S are dissolved in 50 ml of tetrahydrofuran and, while stirring, reacted with 1 g of zinc powder, 2 g of p.toluen sulfonic acid and 2 ml of acetaldehyde. Stirring is continued for 30 minutes at room temperature and the reaction mixture is filtered; the tetrahydrofuran solution being washed by saturated solutions of sodium sulfite, sodium disulfite and sodium chloride respectively, then evaporated to dryness at reduced pressure to give a raw product that is purified by column chromatography as already described; thus obtaining 1.8 g of pure product having formula (I) where X is methyl and Z is benzyl.

Rf. 0.64

I.R.: 3450, 1720, 1660, 1630, 1600, 1550, 1420, 1360, 1340, 1300, 1260, 1240(sh), 1210, 1170, 1150(sh), 1130, 1100, 1070, 1050, 1010, 970, 950, 930, 890, 860, 830 and 800 cm$^{-1}$.

U.V. (CHCl$_3$): 450 nm (E$_1$ $_{cm}$$^{1\%}$ 115); 292 nm (E$_1$ $_{cm}$$^{1\%}$ 291); 240 nm (E$_1$ $_{cm}$$^{1\%}$ 306).

EXAMPLE 40

When in the reaction described in Example 1 acetaldehyde is replaced by 2-hexenal (trans), a product is obtained having formula (I) where X is 1-hexen-1-yl and Z is n-propyl.

Rf. 0.81

I.R. 3400, 1710, 1605, 1550, 1525, 1295, 1250, 1220, 1160, 1125, 1060, 1040, 1010, 970, 890, 810 and 800 cm$^{-1}$.

EXAMPLE 41

5 g of 3-ethanolamino-rifamycin S are dissolved in 50 ml of tetrahydrofuran, then 2 g of zinc powder, 3 g of p-toluensulfonic acid are added while stirring; after 5' at room temperature, 2 ml of acetaldehyde are added. The reaction mixture is stirred 4 hours at room temperature and filtered. The tetrahydrofuran solution is washed with saturated solution of sodium sulfite, sodium disulfite and sodium chloride respectively, then dried and evaporated to dryness at reduced pressure and crystallized from benzene to give 0.9 g of orange crystals of compound having formula (I), where X is methyl and Z is 2-hydroxy-ethyl.

Rf. 0.65

I.R. 3450, 1710, 1655, 1635, 1590, 1550, 1320, 1260, 1210, 1160, 1100, 1065, 1055, 1015, 970, 940, 930, 895, 870 and 800 cm$^{-1}$.

EXAMPLE 42

1.7 g of 3-tetrahydrofurfuryl-rifamycin S are dissolved in 30 ml of tetrahydrofuran and reacted, while stirring at room temperature, with 1 g of zinc powder, 2 g of p-toluen-sulfonic acid and 1 ml of acetaldehyde. After filtering the tetrahydrofuran solution is washed as above described and evaporated to dryness. The product such obtained is purified by column chromatography as already described to give 0.4 g of orange crystals of pure compound having formula (I), where X is methyl and Z is tetrahydrofurfuryl.

Rf. 0.78

I.R. 3450, 1715, 1660, 1630, 1590, 1550, 1330, 1260, 1210, 1165, 1065, 1015, 970, 900, 870 and 800 cm$^{-1}$.

What we claim is:

1. A rifamycin compound selected from the group consisting of compounds having the formula:

(I)

wherein:
Y is —H or —COCH$_3$,
Z is allyl, hydroxyethyl, cycloalkyl having from 3 to 6 carbon atoms, benzyl, phenyl, chlorophenyl and tetrahydrofurfuryl,
X is hydrogen, alkyl having from 1 to 5 carbon atoms, cyclohexyl, alkenyl, having from 3 to 6 carbon atoms, cycloalkenyl having 6 carbon atoms, phenyl, phenyl substituted with a methoxy group, un-substituted arylalkenyl having 8 carbon atoms, a 5 membered heterocycle having one heteroatom selected from the group consisting of O and S, substitution products for the above specified 5 membered heterocycle having substituents selected from the group consisting of halogen, methyl and mixtures thereof, a 6 membered heterocycle having one O-heteroatom; 16, 17, 18, 19 and tetrahydroderivatives thereof; 16, 17, 18, 19, 28, 29 hexahydroderivatives thereof; and corresponding oxidized products having formula (II)

wherein X, Y and Z are as above identified.

2. A process for producing the rifamycin according to claim 1 selected from the group consisting of compounds of formula (I); 16, 17, 18, 19 tetrahydroderivatives thereof, and 16, 17, 18, 19, 28, 29 hexahydroderivatives, thereof wherein: an aldehyde of formula

X - CHO is reacted with a 3-amino-rifamycin S selected from the group consisting of compounds of the formula (III) 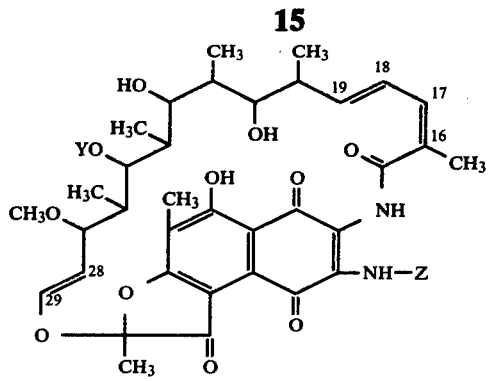

16, 17, 18, 19 and tetrahydroderivatives thereof and 16, 17, 18, 19, 28, 29 hexahydroderivatives thereof, X, Y and Z being as defined in claim 1, in the presence of a reducing agent selected from the group consisting of ascorbic acid, zinc and iron, in an organic solvent selected from the group consisting of dichloromethane, chloroform, tetrahydrofuran, dioxane, dimethylsulfoxide, and N,N-dimethylformamide, at a temperature from 0° C. to +70° C. and for a time from 5 minutes to 3 days.

* * * * *